(12) United States Patent
Vandersall et al.

(10) Patent No.: US 6,977,314 B2
(45) Date of Patent: Dec. 20, 2005

(54) METAL-DOPED SULFONATED ION EXCHANGE RESIN CATALYSTS

(75) Inventors: Mark Thornton Vandersall, Jamison, PA (US); Rudolf Alfred Weinand, Heppenheim (DE)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 10/308,477

(22) Filed: Dec. 3, 2002

(65) Prior Publication Data

US 2003/0139629 A1 Jul. 24, 2003

Related U.S. Application Data

(60) Provisional application No. 60/342,021, filed on Dec. 19, 2001.

(51) Int. Cl.$^7$ .................................. C07C 45/73
(52) U.S. Cl. ................. 568/388; 568/392; 568/396; 568/404
(58) Field of Search ................. 568/388, 392, 568/396, 404

(56) References Cited

U.S. PATENT DOCUMENTS

| | | | |
|---|---|---|---|
| 3,158,583 A | 11/1964 | Corte et al. ................. 260/2.2 |
| 3,574,763 A | * 4/1971 | Wollner et al. .............. 568/396 |
| 3,953,517 A | 4/1976 | Schmitt et al. .............. 260/593 |
| 4,330,679 A | 5/1982 | Kohler et al. ............... 568/697 |
| 4,382,124 A | * 5/1983 | Meitzner et al. ............. 521/38 |
| 5,395,981 A | 3/1995 | Marker ....................... 568/697 |
| 5,583,263 A | * 12/1996 | Muthusamy et al. ....... 568/396 |
| 6,008,416 A | * 12/1999 | Lawson et al. ............. 568/396 |
| 6,235,673 B1 | 5/2001 | Lee et al. .................... 502/159 |

FOREIGN PATENT DOCUMENTS

| | | |
|---|---|---|
| EP | 1191113 A | 5/1970 |
| EP | 1227977 A | 4/1971 |
| EP | 1280368 A | 4/1972 |
| EP | 0539058 A | 4/1993 |

* cited by examiner

*Primary Examiner*—Johann Richter
*Assistant Examiner*—Sikarl A. Witherspoon
(74) *Attorney, Agent, or Firm*—Thomas J. Howell; Witold Andrew Ziarno

(57) ABSTRACT

A method for preparing ketones in greater yield and selectivity compared to previous catalyzed reactions by acid-catalyzed condensation reaction using a metal-doped polysulfonated ion exchange resin catalyst is disclosed. For example, use of polysulfonated ion exchange resins having at least 5.0 milliequivalents sulfonic acid groups/gram catalyst and loaded with metal, such as palladium, provides enhanced yields of methyl isobutyl ketone from the condensation reaction of acetone compared to use of conventional monosulfonated ion exchange resin catalysts.

8 Claims, No Drawings

METAL-DOPED SULFONATED ION EXCHANGE RESIN CATALYSTS

CROSS REFERENCE TO RELATED PATENT APPLICATIONS

This is a non-provisional application of prior pending U.S. provisional application serial No. 60/342,021 filed Dec. 19, 2001.

BACKGROUND

This invention relates to the preparation of ketones having at least 6 carbon atoms by the catalysed condensation reaction of other ketones. In particular the present invention relates to the use of metal-doped polysulfonated ion exchange resin catalysts to provide the desired ketones in greater yield and selectivity compared to the condensation catalysts previously used.

Aldol condensation reactions involve the dimerization of a carbonyl compound (aldehyde or ketone) by the addition of the α-carbon of one carbonyl compound to the carbonyl carbon of another to provide a β-hydroxy carbonyl compound. In the case of the condensation of two ketones in the presence of an acidic catalyst, dehydration usually occurs subsequent to dimerization to provide an α,β-unsaturated ketone; reduction of the double bond using conventional techniques may be used to provide the saturated ketone adduct.

For example, U.S. Pat. No. 6,008,416 discloses a working example of dimerization/dehydration/hydrogenation of acetone to provide mesityl oxide, and ultimately methyl isobutyl ketone (MIBK), by using a monosulfonated acidic catalyst (Amberlyst™ 15 ion exchange resin) loaded with 0.05% palladium. The sulfonic acid group acts as a condensation/dehydration catalyst and the palladium acts as catalyst for hydrogenation of the double bond.

The problem addressed by the present invention is to overcome the deficiencies of prior methods for the preparation of ketones by use of selected catalyst materials to provide enhanced yields and selectivities to desired saturated ketone adducts.

STATEMENT OF INVENTION

The present invention provides a process for preparing ketones having 6 or more carbon atoms comprising contacting a ketone reactant with hydrogen in presence of a polysulfonated ion exchange resin catalyst, wherein the catalyst comprises (a) 1 to 85 percent polymerized crosslinker units, based on dry weight of catalyst; (b) 5.0 to 7.0 milliequivalents sulfonic acid groups per gram, based on dry weight of catalyst; and (c) 0.1 to 2 percent metal ion, based on dry weight of the catalyst, distributed therein and selected from one or more of palladium, platinum, iridium, rhodium, ruthenium, osmium, copper, nickel and zirconium.

In another aspect the present invention provides a polysulfonated ion exchange resin composition comprising (a) 10 to 25 percent polymerized crosslinker units, based on dry weight of ion exchange resin; (b) 5.2 to 6.0 milliequivalents sulfonic acid groups per gram, based on dry weight of ion exchange resin; and (c) 0.5 to 1.5 percent metal ion, based on dry weight of the catalyst, distributed therein and selected from one or more of palladium, platinum, iridium, rhodium, ruthenium, osmium, copper, nickel and zirconium.

DETAILED DESCRIPTION

We have discovered a method for preparing ketones having at least 6 carbon atoms by the catalysed condensation reaction of other ketones in the presence of hydrogen based on the use of metal-doped polysulfonated catalysts to provide the desired ketones in greater yields and selectivity compared to the monosulfonated condensation catalysts used in previous methods.

As used throughout the specification, the following terms shall have the following meanings, unless the context clearly indicates otherwise.

The term "crosslinked polymer matrix" refers to any crosslinked polymeric substrate that is conveniently functionalized to provide polysulfonated aromatic rings; typically the crosslinked polymer matrix is a crosslinked styrenic polymer where the aromatic rings are subjected to polysulfonation conditions to provide catalysts useful in the process of the present invention. The term "copolymer" refers to polymer compositions containing units of two or more different monomers, including positional isomers. The term "crosslinked macroporous copolymer" indicates a polymer or copolymer polymerized from a monomer or mixture of monomers containing at least 1 weight percent (%), based on the total monomer weight, of polyvinyl unsaturated monomer. The term "alkyl (meth)acrylate" refers to either the corresponding acrylate or methacrylate ester; similarly, the term "(meth)acrylic" refers to either acrylic or methacrylic acid and the corresponding derivatives, such as esters or amides. All percentages referred to will be expressed in weight percent (%), based on total weight of polymer or composition involved, unless specified otherwise. The following abbreviations are used herein: g=grams, μm=microns, cm=centimeters, mm=millimeters, m=meters, ml=milliliters, meq/g=milliequivalents/gram, L=liter, 1 bar pressure=$10^5$ Pascal or $10^5$ Pa. Unless otherwise specified, ranges listed are to be read as inclusive and combinable and temperatures are in degrees centigrade (° C.).

Although the metal-doped polysulfonated ion exchange resins may be applied generally to acid-catalyzed condensation reactions that employ strong acid cation exchange resins as the catalyst, their use is particularly advantageous in those condensation reactions where the product is a ketone derived from the dimerization/dehydration/hydrogenation reaction of other ketone reactant substrates.

Using the process of the present invention, ketone reactants represented by compound A (see Equation 1) are dimerized in the presence of a polysulfonated catalyst B. As the dimerized β-hydroxy ketone adduct C is formed it undergoes dehydration to the α,β-unsaturated ketone derivative D (see Equation 2). In the presence of hydrogen and the metal-dope polysulfonated catalyst B, the α,β-unsaturated ketone derivative D is converted to the saturated ketone adduct E (see Equation 3).

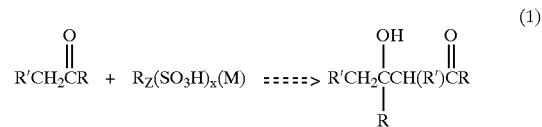

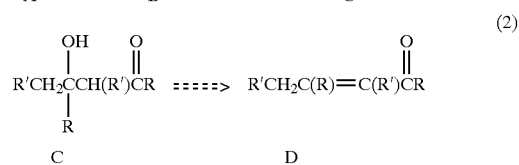

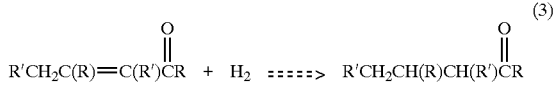

(3)

R'=phenyl, H or $C_1$–$C_4$ alkyl
R=$C_1$–$C_4$ alkyl or phenyl
$R_Z$=crosslinked polymer matrix
$(SO_3H)_x$=polysulfonic acid groups, where x=>1<2, representing average number of sulfonic groups per aromatic ring
M=metal or metal ion selected from Pd, Pt, Ir, Rh, Ru, Os, Cu, Ni, Zr The acid catalysts useful in the process of the present invention are strong acid cation exchange resins having polysulfonate functionality; that is, the crosslinked polymer matrix supporting the catalyst sites contains aromatic rings having more than one sulfonic acid group per aromatic ring. Typically at least 10%, preferably at least 15% and more preferably at least 20% of the aromatic rings contain more than one sulfonic acid group per aromatic ring.

The polysulfonated cation exchange resins useful in the process of the present invention may be in the form of gel or macroporous beads. Preferably, the polysulfonated cation exchange resin catalysts are in the form of macroporous spherical beads having average particle diameters from 100 µm to 2 mm, preferably from 150 µm to 1.5 mm and more preferably from 250 to µm to 1 mm; have a sulfonic acid group content of 5.0 to 7.0, preferably 5.1 to 6.5 and more preferably 5.2 to 6.0 meq/g, based on dry weight of polysulfonated cation exchange resin; loaded with 0.1 to 2%, preferably 0.5 to 1.5% and more preferably 0.8 to 1.2%, of metal or metal ion, based on dry weight of polysulfonated cation exchange resin; typically possess a surface area from 10 to 100, preferably 15 to 75 and more preferably 20 to 50 square meters/gram ($m^2$/g); and a total porosity of 0.1 to 0.9, preferably 0.2 to 0.7 and more preferably 0.25 to 0.5 cubic centimeter pores per gram polymer ($cm^3$/g), with an average pore diameter of 50 to 2,500 Ångstrom units and preferably 150 to 1000 Ångstrom units. Porosities are defined according to IUPAC (International Union of Pure and Applied Chemistry) nomenclature as follows:

---

Microporosity = pores less than 20 Ångstrom units
Mesoporosity = pores between 20 and 500 Ångstrom units
Macroporosity = pores greater than 500 Ångstrom units

---

With regard to the surface area and porosity of the polysulfonated cation exchange resin catalyst, if the surface area is too low (below about 10 $m^2$/g), the hydrogenation activity of the catalyst will be affected and selectivity to the desired saturated ketone adduct will be decreased. In cases where the pore size decreases and the surface areas are in excess of about 100 $m^2$/g, the reaction sequence will suffer from poor diffusion of reactants throughout the catalyst bed, resulting in lower productivity of the desired saturated ketone adduct.

The polysulfonated cation exchange resins are typically prepared from crosslinked macroporous copolymers, such as those described in U.S. Pat. No. 4,382,124, in which porosity is introduced into the copolymer beads by suspension-polymerization in the presence of a porogen (also known as "phase extender" or "precipitant"), that is, a solvent for the monomer but a non-solvent for the polymer.

A typical crosslinked macroporous copolymer preparation, for example, may include preparation of a continuous aqueous phase solution containing suspension aids (such as dispersants, protective colloids and buffers) followed by mixing with a monomer mixture containing 1 to 85% polyvinylaromatic monomer, free-radical initiator and typically 0.2 to 5, preferably 0.3 to 3 and more preferably 0.4 to 1, parts porogen (such as toluene, xylenes, ($C_4$–$C_{10}$)-alkanols, ($C_6$–$C_{12}$)-saturated hydrocarbons or polyalkylene glycols) per one part monomer. The mixture of monomers and porogen is then polymerized at elevated temperature and the porogen is subsequently removed from the resulting polymer beads by various means; for example, toluene, xylene and ($C_4$–$C_{10}$)alcohols may be removed by distillation or solvent washing, and polyalkylene glycols by water washing. The resulting macroporous copolymer is then isolated by conventional means, such as dewatering followed by drying.

Suitable polyvinylaromatic monomers that may be used in the preparation of the crosslinked copolymers include, for example, one or more monomer selected from the group consisting of divinylbenzene, trivinylbenzene, divinyltoluene, divinylnaphthalene and divinylxylene; it is understood that any of the various positional isomers of each of the aforementioned crosslinkers is suitable; preferably the polyvinylaromatic monomer is divinylbenzene. Typically the crosslinked copolymer comprises 1 to 85%, preferably 5 to 55% and more preferably 10 to 25%, polyvinylaromatic monomer units.

Optionally, non-aromatic crosslinking monomers, such as ethyleneglycol diacrylate, ethyleneglycol dimethacrylate, trimethylolpropane triacrylate, trimethylolpropane trimethacrylate, diethyleneglycol divinyl ether and trivinylcyclohexane, may also be used in addition to the polyvinylaromatic crosslinker. When used, the non-aromatic crosslinking monomers typically comprise as polymerized units, from zero to 10%, preferably from zero to 5%, and more preferably from zero to 2% of the macroporous polymer, based on the total monomer weight used to form the macroporous copolymer.

Suitable monounsaturated vinylaromatic monomers that may be used in the preparation of crosslinked copolymers include, for example, styrene, α-methylstyrene, ($C_1$–$C_4$) alkyl-substituted styrenes, halo-substituted styrenes (such as dibromostyrene and tribromostyrene), vinylnaphthalene and vinylanthracene; preferably the monounsaturated vinylaromatic monomer is selected from one or more of the group consisting of styrene and ($C_1$–$C_4$)alkyl-substituted styrenes. Included among the suitable ($C_1$–$C_4$)alkyl-substituted styrenes are, for example, ethylvinylbenzenes, vinyltoluenes, diethylstyrenes, ethylmethylstyrenes and dimethylstyrenes; it is understood that any of the various positional isomers of each of the aforementioned vinylaromatic monomers is suitable. Preferably the copolymer comprises 15 to 99%, and more preferably 75 to 90%, monounsaturated vinylaromatic monomer units.

Optionally, non-aromatic monounsaturated vinyl monomers, such as aliphatic unsaturated monomers, for example, vinyl chloride, acrylonitrile, (meth)acrylic acids and alkyl (meth)acrylates may also be used in addition to the vinylaromatic monomer. When used, the non-aromatic monounsaturated vinyl monomers typically comprise as polymerized units, from zero to 10%, preferably from zero to 5%, and more preferably from zero to 2% of the macroporous copolymer, based on the total monomer weight used to form the macroporous copolymer.

Porogens useful for preparing macroporous copolymers include hydrophobic porogens, such as ($C_7$–$C_{10}$)aromatic hydrocarbons and ($C_6$–$C_{12}$)saturated hydrocarbons; and hydrophilic porogens, such as ($C_4$–$C_{10}$)alkanols and polyalkylene glycols. Suitable ($C_7$–$C_{10}$)aromatic hydrocarbons include, for example, one or more of toluene, ethylbenzene, ortho-xylene, meta-xylene and para-xylene; it is understood that any of the various positional isomers of each of the aforementioned hydrocarbons is suitable. Preferably the aromatic hydrocarbon is toluene or xylene or a mixture of xylenes or a mixture of toluene and xylene. Suitable ($C_6$–$C_{12}$)saturated hydrocarbons include, for example, one or more of hexane, heptane and isooctane; preferably, the saturated hydrocarbon is isooctane. Suitable ($C_4$–$C_{10}$) alkanols include, for example, one or more of isobutyl alcohol, tert-amyl alcohol, n-amyl alcohol, isoamyl alcohol, methyl isobutyl carbinol (4-methyl-2-pentanol), hexanols and octanols; preferably, the alkanol is selected from one or more ($C_5$–$C_8$)alkanols, such as, methyl isobutyl carbinol and octanol.

Polymerization initiators useful in preparing copolymers include monomer-soluble initiators such as peroxides, hydroperoxides and related initiators; for example benzoyl peroxide, tert-butyl hydroperoxide, cumene peroxide, tetralin peroxide, acetyl peroxide, caproyl peroxide, tert-butyl peroctoate (also known as tert-butylperoxy-2-ethylhexanoate), tert-amyl peroctoate, tert-butyl perbenzoate, tert-butyl diperphthalate, dicyclohexyl peroxydicarbonate, di(4-tert-butylcyclohexyl) peroxydicarbonate and methyl ethyl ketone peroxide. Also useful are azo initiators such as azodiisobutyronitrile, azodiisobutyramide, 2,2'-azo-bis(2,4-dimethylvaleronitrile), azo-bis($\alpha$-methylbutyronitrile) and dimethyl-, diethyl- or dibutyl azo-bis(methylvalerate). Preferred peroxide initiators are diacyl peroxides, such as benzoyl peroxide, and peroxyesters, such as tert-butyl peroctoate and tert-butyl perbenzoate; more preferably, the initiator is benzoyl peroxide. Typical use levels of peroxide initiator are 0.3% to 5%, preferably from 0.5 to 3% and more preferably from 0.7 to 2%, based on the total weight of vinyl monomers.

Preferably, the crosslinked copolymers are selected from the group consisting of divinylbenzene copolymer, styrene-divinylbenzene copolymer, divinylbenzene-ethylvinylbenzene copolymer and styrene-ethylvinylbenzene-divinylbenzene copolymer, for use as substrates for the polysulfonated catalysts used in the process of the present invention.

These crosslinked copolymers may be functionalized with strong-acid functional groups according to conventional processes for polysulfonation known to those having ordinary skill in the art, as for example, sulfonation with sulfur trioxide ($SO_3$), fuming sulfuric acid or oleum (concentrated sulfuric acid containing sulfur trioxide) and chlorosulfonic acid; alternatively, monosulfonated cation exchange resin polymeres may also be subjected to conventional polysulfonation conditions to provide the polysulfonated cation exchange resin catalysts.

The polysulfonated cation exchange resins are typically loaded with the desired metal ion by contacting an aqueous solution of the metal ion with the hydrogen form of the cation exchange resin in a batch or column mode. Typically the metal ion will be provided in the form a metal salt, such as, for example, chlorides, bromides, nitrates, sulphates and acetates. The loaded cation exchange resin is then rinsed free of residual salts or acid. The amount of metal salt used is chosen such that the metal or metal ion will ultimately be present in an amount of about 1 to 15 g/L (0.1 to 2% loading), preferably about 4 to 10 g/L (0.5 to 1.5% loading) and more preferably about 6 to 8 g/L (0.8 to 1.2% loading) of cation exchange resin, and can be determined by conventional analytical test methods. At metal concentrations greater than about 2% loading (based on dry weight of catalyst) on the polysulfonated catalyst, reduction of the carbonyl group may occur and detract from the overall yield of desired ketone adduct (E in Equation 3). Metal ions suitable for use as part of the polysulfonated catalysts useful in the process of the present invention include, for example, palladium (Pd), platinum (Pt), rhodium (Rh), iridium (Ir), ruthenium (Ru), osmium (Os), copper (Cu), nickel (Ni) and zirconium (Zr). Preferably, the polysulfonated cation exchange resin catalysts contain 0.5 to 1.5% palladium, based on dry weight of the catalyst.

With regard to the loading level of metal on the polysulfonated cation exchange resin catalyst, if the metal loading level is too low (below about 0.1%), the catalyst will not have sufficient activity for the hydrogenation reaction and selectivity to the saturated ketone adduct will be unsatisfactory. If the metal loading level is too high (above about 2%), the hydrogenation activity will be too high and lead to reduced yields of the desired saturated adduct.

Representative of loading of the polysulfonated cation exchange resin with metal is the following description. For example, 1 liter of polysulfonated cation ion exchange resin in hydrogen (H) form, is poured into a solution of 10–50 g of palladium nitrate in 0.5–2 liters of distilled water and the palladium is allowed to absorb onto the cation exchange resin for about 1 to 4 hours and then the solution is decanted from the resin. Alternatively, the polysulfonated cation exchange resin may be loaded with metal by passing an aqueous solution of the metal salt through a column of the polysulfonated cation exchange resin until a desired level of metal ion has been retained by the resin—this is followed by thorough washing with water to remove residual salts and acid generated during the loading process.

Preferably, the catalyst is prepared by reducing a polysulfonated ion exchange resin containing metal ions to deposit the metal in elemental form in the catalyst. In this case the loaded resin may be subjected to 'activation' (reduction) by exposing the loaded resin to hydrogen (typically at room temperature and low partial pressures of hydrogen, for example, less than 1 bar). Alternatively, the activation may be conducted at temperatures up to about 120° C. and at hydrogen pressures of about 2 to 50 bar. The loaded catalyst containing the metal in reduced form may then be used as desired in the condensation reaction.

Alternatively, the loaded resin (metal in ionic form) may be 'activated' to the reduced metal form just prior to use in a condensation reaction. For example, when the condensation reaction involves the dimerization of acetone to MIBK, acetone is typically pumped through a column reactor containing the metal-ion loaded polysulfonated catalyst at a liquid hourly space velocity (LHSV) of about 0.5 $h^{-1}$ (that is, 0.5 volumes of acetone per volume of catalyst resin per hour). The pressure of the reactor is then increased to about 30 bar with hydrogen. After establishing a desired hydrogen flow through the reactor, the temperature is then increased to about 90° C. and maintained for about 10–16 hours. The reactor may then be heated to a desired reaction temperature, typically 110 to 150° C., with the desired acetone and hydrogen flows to initiate the conversion of acetone to MIBK.

When Pd, Pt, Rh, Ir, Ru or Os are used as the metal component of the catalyst it is preferable that the loaded resin be activated to the reduced metal form prior to being used in the condensation reaction.

In addition to the condensation reactions of the ketones described herein, the metal-doped polysulfonated cation exchange resin catalysts may be used to promote etherification of isolefins and alcohols to high octane oxygenate additives (ethers) for motor fuels, such as is described in U.S. Pat. Nos. 4,330,679 and 5,395,981.

In a preferred embodiment of the present invention, the metal-doped polysulfonated cation exchange resin catalyst is in the physical form of beads contained in a vessel, the beads forming a bed of the catalyst. A feed stream of ketone reactant, such as acetone, is brought into contact with the catalyst bed in the presence of hydrogen (as a separate feed stream) for a sufficient time and temperature for the condensation reaction of the ketone to occur. The condensed liquid stream, containing reaction products (saturated ketone adduct), byproducts (unsaturated ketone adduct) and any unreacted ketone reactant which may be present, is separated from the catalyst bed, and desired ketone adduct is recovered from the liquid stream by conventional separations means (such as distillation). One of ordinary skill in the art will be able to choose appropriate conditions, such as (1) batch operation, for example, in which the catalyst bed is loaded with the liquid stream in the presence of hydrogen, followed by removal of the liquid stream from the catalyst after the desired reaction has occurred, or (2) the more preferred continuous operation, for example, where the liquid stream is fed continuously into one end of a column reactor (with hydrogen) at a rate that allows sufficient residence time in the catalyst bed for the desired reaction to occur, with the condensed liquid stream being removed continuously from the other end of the bed. Similarly, the reaction equipment, the choice of upflow or downflow for the direction of passage of the reactant streams through the bed, the reaction time and temperature, the particular reactants, and the method of recovering the ketone adduct, are readily selected based upon the guidance provided herein and the knowledge available to one of ordinary skill in the art.

Typically, the temperatures and pressures inside the column reactor are selected so that the ketone reactant is at its boiling point in the catalyst bed. Variation of temperature/pressure of the ketone reactant is used to provide the desired combination of reaction temperature and conditions such that the condensation reaction takes place in the liquid phase in the catalyst bed. Conditions may be varied to provide gas phase conditions with the catalyst bed; however, it is preferred that the conditions are such that the condensation reaction is conducted in the liquid phase.

The metal-doped polysulfonated cation exchange resin catalysts of the present invention may be used in condensation reactions where the ketone reactant and hydrogen are contacted under batch reaction conditions or under continuous reaction conditions. In one embodiment of the invention the process is a continuous process based on a catalytic distillation process with the introduction of the ketone reactant being into the bottom of a column reactor immediately above a reboiler stage; in this case the product fraction or stream is withdrawn continuously from the reboiler portion of the distillation apparatus for further processing (see U.S. Pat. No. 6,008,416 for further general and specific details of catalytic distillation processes). Preferably, the ketone reactant to undergo the condensation reaction is fed downward through the catalyst bed and a current of hydrogen is passed through the reaction zone in the same direction. However, other variations of introducing the reactant feed streams may be used, such as co-current and countercurrent hydrogen flow, flooding processes and gaseous-phase processes.

For continuous processes, the amount of catalyst to be used, relative to the amount of reactants, is typically related to the throughput rate of the reactions, as indicated by the LHSV (liquid hourly space velocity) or liquid flow rate of reactants relative to the volume of catalyst per unit time. Typically, high LHSV are desirable to maximize equipment usage and generation of product; however meeting this objective must be balanced against % conversion of raw materials and % selectivity to the desired product. If the LHSV is too low, production rate of the desired product (space-yield) is diminished and the process may not be economical. If the LHSV is too high, the catalyst activity will be insufficient to provide the desired level of conversion (the process becomes "kinetically limited"). Suitable values of LHSV will typically range from 0.5 and 10 $h^{-1}$, preferably from 1 to 8 $h^{-1}$ and more preferably from 2.5 to 6 $h^{-1}$.

Typically, the ketone reactant is contacted with hydrogen in presence of the catalyst at a temperature of 110 to 170° C. and at a pressure from 1 to 100 bar of hydrogen. Suitable temperatures for conducting the catalyzed condensation reactions of the present invention are from 110 to 170° C., preferably from 120 to 160° C. and more preferably from 130 to 150° C. At the lower temperatures (below about 110° C.), the catalyst does not have sufficient activity to provide desirable conversion and yield. At temperatures above about 170° C., the selectivity of the reaction to the desired saturated ketone adduct decreases, and the catalyst lifetime is adversely affected. In general, the reaction zone of the ketone reactant and hydrogen is maintained at a pressure of 1 to 100 bar of hydrogen, preferably from 5 to 60 bar and more preferably from 10 to 40 bar. Typically, the condensation reaction is conducted at a hydrogen/ketone reactant molar ratio of 0.1 to 1 and preferably from 0.15 to 0.5.

In another embodiment of the invention, the process may be a batch one with the introduction of the ketone reactant into a reactor column at the reboiler section stage of a catalytic distillation apparatus (similar to that described above). The process may then be terminated when a desired product composition of ketone adduct is achieved in the reboiler section. Alternatively, the condensation may be carried out in a batch autoclave reactor for a specified period of time, followed by cooling and recovery of the desired of the ketone adduct by distillation or other conventional means.

Some embodiments of the invention are described in detail in the following Examples. All ratios, parts and percentages are expressed by weight unless otherwise specified, and all reagents used are of good commercial quality unless otherwise specified. Abbreviations used in the Examples and Tables are listed below with the corresponding descriptions:

MIBK = methyl isobutyl ketone (4-methyl-2-pentanone)
LHSV = liquid hourly space velocity ($h^{-1}$)
DVB = divinylbenzene (mixture of meta/para isomers)
$cm^3/g$ = cubic centimeter per gram

EXAMPLE 1

A fixed-bed reactor was used to evaluate various cation exchange resin catalysts for the condensation of acetone to mesityl oxide and ultimately to methyl isobutyl ketone (MIBK). The tubular reactor was in the form of a column with an inner diameter of 10 mm and a length of 45 cm. A catalyst charge of 25 ml of cation exchange resin catalyst was used for each experiment and temperatures were monitored with an adjustable position thermocouple inserted into the reactor. Prior to initiating the condensation reaction, the metal-doped catalysts were activated (reduction of palladium to the metallic form) by pumping acetone through the reactor at a LHSV of 0.5 h$^{-1}$, and adding hydrogen to a pressure of 30 bar. The temperature was then raised to 90° C. and held there for 10–16 hours, before raising the temperature to the desired test temperature (130–150° C.) and starting the reactant feeds (acetone and hydrogen). Typically the reactor was run at design conditions for a period of time (typically 1–2 days) to ensure steady-state operation, and then the effluent stream was sampled for analysis.

For condensation reactions run at LHSV of 2.8, the ketone reactant feed stream was added at 70 ml/hour and the hydrogen at 4.1 L/hour; for LHSV of 5.6, the ketone reactant feed rate was 140 ml/hour and hydrogen flow at 5.8 L/hour.

The ketone reactant feed stream contained 96% acetone, 1% isopropanol, about 2% C$_9$-hydrocarbon impurities and 1% water. The hydrogen stream was fed at a rate to provide a hydrogen/acetone molar ratio of 0.19/1. Condensed reaction product streams were analyzed by conventional gas chromatographic analyses to determine % acetone conversion, % selectivity to MIBK and overall MIBK yield. MIBK productivity was expressed as "ml MIBK product per ml catalyst per hour." In addition to maximizing conversion and selectivity of the basic condensation/hydrogenation reaction, a high "MIBK productivity" value is desirable, preferably greater than 1.0 and more preferably greater than 1.4.

Three catalysts were evaluated and the results are summarized in Tables 1 and 2.

Catalyst 1 (comparative): Monosulfonated styrene/DVB (12%) copolymer with 4.8 meq/g sulfonic acid capacity, % palladium=0.7% based on dry weight of catalyst, % moisture=47–54%, average particle size=0.85–1.0 mm, surface area=35 m$^2$/g, porosity=0.24 cm$^3$/g, average pore diameter=150 Ångstrom units.

Catalyst 2: Polysulfonated styrene/DVB (18%) copolymer with 5.2 meq/g sulfonic acid capacity, % moisture= 51–57%, % palladium=0.75% based on dry weight of catalyst, average particle size=0.7–0.95 mm, surface area= 45 m$^2$/g, porosity=0.34 cm$^3$/g, average pore diameter=240 Ångstrom units.

Catalyst 3: Polysulfonated styrene/DVB (18%) copolymer with 5.2 meq/g sulfonic acid capacity, % moisture= 51–57%, % palladium=1.0% based on dry weight of catalyst, average particle size=0.7–0.95 mm, surface area= 45 m$^2$/g, porosity=0.34 cm$^3$/g, average pore diameter=240 Ångstrom units.

TABLE 1

MIBK Production @ 130° C.

|  | % Conv$^a$ | % Select$^b$ | % Yield$^c$ | MIBK Productivity$^d$ |
|---|---|---|---|---|
| LHSV = 2.8 h$^{-1}$ | | | | |
| Catalyst 1 (comp) | 39.9 | 91.2 | 36.4 | 0.84 |
| Rel* to Cat 1 | (1.0) | (1.0) | (1.0) | (1.0) |
| Catalyst 2 | 44.0 | 98.2 | 43.2 | 0.99 |
| Rel* to Cat 1 | 1.10 | 1.08 | 1.19 | 1.18 |
| Catalyst 3 | 39.4 | 101.8 | 40.1 | 0.92 |
| Rel* to Cat 1 | 0.99 | 1.12 | 1.10 | 1.10 |
| LHSV = 5.6 h$^{-1}$ | | | | |
| Catalyst 1 (comp) | 32.6 | 85.6 | 27.9 | 1.28 |
| Rel* to Cat 1 | (1.0) | (1.0) | (1.0) | (1.0) |
| Catalyst 2 | 35.7 | 95.9 | 34.2 | 1.57 |
| Rel* to Cat 1 | 1.10 | 1.12 | 1.23 | 1.23 |
| Catalyst 3 | 38.4 | 93.7 | 36.0 | 1.65 |
| Rel* to Cat 1 | 1.18 | 1.09 | 1.29 | 1.29 |

$^a$acetone conversion
$^b$selectivity to MIBK product
$^c$yield of MIBK based on converted acetone
$^d$efficiency of overall reaction (ml MIBK per ml catalyst per hour)
*relative increase in conversion, selectivity, yield and productivity compared to Catalyst 1

TABLE 2

MIBK Production @ 140° C./150° C. and LHSV = 5.6 h$^{-1}$

|  | % Conv$^a$ | % Select$^b$ | % Yield$^c$ | MIBK Productivity$^d$ |
|---|---|---|---|---|
| Temp = 140° C. | | | | |
| Catalyst 1 (comp) | [34.8]** | [84.2]** | [29.3]** | [1.34]** |
| Rel* to Cat 1 | (1.0) | (1.0) | (1.0) | (1.0) |
| Catalyst 2 | 37.6 | 94.6 | 35.5 | 1.63 |
| Rel* to Cat 1 | 1.08 | 1.12 | 1.21 | 1.22 |
| Temp = 150° C. | | | | |
| Catalyst 1 (comp) | 37.1 | 82.9 | 30.7 | 1.41 |
| Rel* to Cat 1 | (1.0) | (1.0) | (1.0) | (1.0) |
| Catalyst 2 | 39.3 | 93.2 | 36.6 | 1.68 |
| Rel* to Cat 1 | 1.06 | 1.12 | 1.19 | 1.19 |

$^a$acetone conversion
$^b$selectivity to MIBK product
$^c$yield of MIBK based on converted acetone
$^d$efficiency of overall reaction (ml MIBK per ml catalyst per hour)
*relative increase in conversion, selectivity, yield and productivity compared to Catalyst 1
**estimated by interpolation of data at 130° C. and 150° C.

In the six instances where the polysulfonated Catalysts 2 or 3 can be compared directly to the monosulfonated catalyst (Catalyst 1), there is an average increase in acetone conversion of about 8%, an average increase in % selectivity to MIBK of about 11% and an average increase in overall MIBK yield and MIBK productivity of about 20% based on use of the metal-doped polysulfonated catalysts of the present invention.

We claim:

1. A process for preparing ketones having 6 or more carbon atoms comprising contacting a ketone reactant with hydrogen in presence of a polysulfonated ion exchange resin catalyst, wherein the catalyst comprises:

(a) 1 to 85 percent polymerized crosslinker units, based on dry weight of catalyst;

(b) 5.0 to 7.0 milliequivalents sulfonic acid groups per gram, based on dry weight of catalyst; and (c) 0.1 to 2 percent metal ion, based on dry weight of the catalyst, distributed therein and selected from one or more of palladium, platinum, iridium, rhodium, ruthenium, osmium, copper, nickel and zirconium.

2. The process of claim 1 wherein the catalyst is prepared by reducing a polysulfonated ion exchange resin containing metal ions to deposit the metal in elemental form in the catalyst.

3. The process of claim 1 wherein the ketone reactant is contacted with hydrogen in presence of the catalyst at a temperature of 110 to 170° C. and at a pressure from 1 to 100 bar.

4. The process of claim 1 wherein the catalyst comprises 5.2 to 6.0 milliequivalents sulfonic acid groups per gram, based on dry weight of catalyst.

5. The process of claim 1 wherein the catalyst comprises 0.5 to 1.5 percent palladium, based on dry weight of the catalyst.

6. The process of claim 1 wherein the ketone reactant and hydrogen are contacted under continuous reaction conditions.

7. The process of claim 1 wherein the polysulfonated ion exchange resin catalyst is in the form of macroporous beads having a total porosity of 0.1 to 0.9 cubic centimeters per gram and a surface area of 10 to 100 square meters per gram, based on dry weight of the catalyst.

8. The process of claim 7 wherein the surface area of the catalyst is from 20 to 50 square meters per gram, based on dry weight of the catalyst.

* * * * *